United States Patent
Harding et al.

(10) Patent No.: US 6,261,519 B1
(45) Date of Patent: Jul. 17, 2001

(54) MEDICAL DIAGNOSTIC DEVICE WITH ENOUGH-SAMPLE INDICATOR

(75) Inventors: Ian A. Harding, San Mateo; Robert Justice Shartle, Livermore; Xiang Jennifer Zheng, Fremont; Philip John Cizdziel, San Jose, all of CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/356,248

(22) Filed: Jul. 16, 1999

Related U.S. Application Data
(60) Provisional application No. 60/093,421, filed on Jul. 20, 1998.

(51) Int. Cl.[7] ................................................. G01N 33/48
(52) U.S. Cl. .............................. 422/58; 422/61; 436/164; 436/169; 436/177; 436/178; 436/69
(58) Field of Search ................................. 422/56, 58, 61, 422/82.05, 100, 102, 103; 436/164, 165, 169, 171, 172, 177, 178, 69

(56) References Cited

U.S. PATENT DOCUMENTS

| | | | |
|---|---|---|---|
| 3,620,676 | 11/1971 | Davis | 23/253 |
| 3,640,267 | 2/1972 | Hurtig et al. | 128/2 |
| 4,088,448 | 5/1978 | Lilja et al. | 23/259 |
| 4,426,451 | 1/1984 | Columbus | 436/518 |
| 4,847,209 | 7/1989 | Lewis et al. | 436/533 |
| 4,868,129 | 9/1989 | Gibbons et al. | 436/179 |
| 5,100,620 | * 3/1992 | Brenneman | 422/58 |
| 5,104,813 | 4/1992 | Besemer et al. | 436/179 |
| 5,208,163 | 5/1993 | Charlton et al. | 436/63 |
| 5,230,866 | 7/1993 | Shartle et al. | 422/103 |
| 5,366,902 | * 11/1994 | Cox et al. | 422/58 |
| 5,472,603 | 12/1995 | Schembri | 210/380 |
| 5,627,041 | 5/1997 | Shartle | 435/7.24 |
| 5,700,695 | 12/1997 | Yassinzadeh et al. | 436/180 |
| 5,736,404 | 4/1998 | Yassinzadeh et al. | 436/52 |
| 5,827,681 | * 10/1998 | Krug et al. | 422/61 |

FOREIGN PATENT DOCUMENTS

| | | |
|---|---|---|
| 0 803 288 | 4/1997 | (EP) . |
| WO 94/02850 | 2/1994 | (WO) . |

* cited by examiner

Primary Examiner—Lyle A. Alexander

(57) ABSTRACT

A fluidic medical diagnostic device permits measurement of analyte concentration or a property of a biological fluid, particularly the coagulation time of blood. The device has at one end a sample port for introducing a sample and at the other end a bladder for drawing the sample to a measurement area. A first channel carries the sample from the sample port to the measurement area, and a stop junction, between the measurement area and bladder, halts the sample flow. A second channel, which runs from the first channel to an edge of the device, determines whether the sample volume is sufficient to permit an accurate measurement. The desired measurement can be made by placing the device into a meter, which measures a physical property of the sample, typically optical transmittance, after it has interacted with one or more reagents on the device.

19 Claims, 8 Drawing Sheets

MEDICAL DIAGNOSTIC DEVICE WITH ENOUGH-SAMPLE INDICATOR

CROSS-REFERENCE TO PRIOR PROVISIONAL APPLICATION

This application claims the benefit of U.S. Provisional Application No. 60/093,421, filed Jul. 20, 1998.

BACKGROUND OF THE INVENTION

1. Field of the Invention

This invention relates to a fluidic medical diagnostic device for measuring the concentration of an analyte in or a property of a biological fluid.

2. Description of the Related Art

A variety of medical diagnostic procedures involve tests on biological fluids, such as blood, urine, or saliva, and are based on a change in a physical characteristic of such a fluid or an element of the fluid, such as blood serum. The characteristic can be an electrical, magnetic, fluidic, or optical property. When an optical property is monitored, these procedures may make use of a transparent or translucent device to contain the biological fluid and a reagent. A change in light absorption of the fluid can be related to an analyte concentration in, or property of, the fluid. Typically, a light source is located adjacent to one surface of the device and a detector is adjacent to the opposite surface. The detector measures light transmitted through a fluid sample. Alternatively, the light source and detector can be on the same side of the device, in which case the detector measures light scattered and/or reflected by the sample. Finally, a reflector may be located adjacent to the opposite surface. A device of this latter type, in which light is first transmitted through the sample area, then reflected through a second time, is called a "transflectance" device. References to "light" throughout this specification and the appended claims should be understood to include the infrared and ultraviolet spectra, as well as the visible. References to "absorption" are meant to refer to the reduction in intensity as a light beam passes through a medium; thus, it encompasses both "true" absorption and scattering.

An example of a transparent test device is described in Wells et al. WO94/02850, published on Feb. 3, 1994. Their device comprises a sealed housing, which is transparent or translucent, impervious, and rigid or semi-rigid. An assay material is contained within the housing, together with one or more assay reagents at predetermined sites. The housing is opened and the sample introduced just before conducting the assay. The combination of assay reagents and analyte in the sample results in a change in optical properties, such as color, of selected reagents at the end of the assay. The results can be read visually or with an optical instrument.

U.S. Pat. No. 3,620,676, issued on Nov. 16, 1971 to Davis, discloses a calorimetric indicator for liquids. The indicator includes a "half-bulb cavity", which is compressible. The bulb is compressed and released to form a suction that draws fluid from a source, through a half-tubular cavity that has an indicator imprinted on its wall. The only controls on fluid flow into the indicator are how much the bulb is compressed and how long the indicator inlet is immersed in the source, while the bulb is released.

U.S. Pat. No. 3,640,267, issued on Feb. 8, 1972 to Hurtig et al., discloses a container for collecting samples of body fluid that includes a chamber that has resilient, collapsible walls. The walls are squeezed before the container inlet is placed into the fluid being collected. When released, the walls are restored to their uncollapsed condition, drawing fluid into and through the inlet. As with the Davis device, discussed above, control of fluid flow into the indicator is very limited.

U.S. Pat. No. 4,088,448, issued on May 9, 1978 to Lilja et al., discloses a cuvette, which permits optical analysis of a sample mixed with a reagent. The reagent is coated on the walls of a cavity, which is then filled with a liquid sample. The sample mixes with the reagent to cause an optically-detectable change U.S. Pat. Nos. 4,426,451; 4,868,129; 5,104,813; and 5,230,866 disclose various devices for diluting and/or analyzing biological fluid samples. The devices include a "stop flow junction" to control the flow of the sample. The junction consists of an abrupt change in the cross-sectional area of a flow channel. Typically, the junction is formed when a small-diameter capillary channel enters a larger channel. The stop junction creates a back pressure that stops the normal blood flow until some additional pressure, such as hydrostatic pressure, acts to cause the sample to break through the junction into the larger channel.

U.S. Pat. No. 5,627,041, issued on May 6, 1997 to Shartle et al., discloses a diagnostic device that includes a stop junction, and the force that causes sample to break through the junction is a centrifugal force provided by rotating the device.

European Patent Application EP 0 803 288, of Naka et al., published on Oct. 29, 1997, discloses a device and method for analyzing a sample that includes drawing the sample into the device by suction, then reacting the sample with a reagent in an analytical section. Analysis is done by optical or electrochemical means. In alternate embodiments, there are multiple analytical sections and/or a bypass channel. The flow among these sections is balanced without using stop junctions. FIG. 9 of Naka et al. depicts a "liquid pooling portion" at the sample inlet and an air vent passage branching from the drawing channel. These two elements, in combination, permit a two-stage process for introducing the sample to the analytical section.

U.S. Pat. No. 5,700,695, issued on Dec. 23, 1997 to Yassinzadeh et al., discloses an apparatus for collecting and manipulating a biological fluid that uses a "thermal pressure chamber" to provide the driving force for moving the sample through the apparatus.

U.S. Pat. No. 5,736,404, issued on Apr. 7, 1998, to Yassinzadeh et al., discloses a method for determining the coagulation time of a blood sample that involves causing an end of the sample to oscillate within a passageway. The oscillating motion is caused by alternately increasing and decreasing the pressure of the sample.

U.S. Pat. No. 5,208,163, issued on May 6, 1993 to Charlton et al., discloses a sample analysis device that includes a metering chamber and capillary that allows an operator to determine that sample has been applied in excess of the amount needed for the measurement.

SUMMARY OF THE INVENTION

The present invention provides a fluidic diagnostic device for measuring an analyte concentration or property of a biological fluid. The device comprises a first layer and second layer at least one of which has a resilient region over at least part of its area, separated by an intermediate layer, in which cutouts in the intermediate layer form, with the first and second layers, a) a sample port for introducing a sample of the biological fluid into the device;

b) a measurement area, in which a physical parameter of the sample is measured and related to the analyte concentration or property of the fluid;

c) a first channel, having a first end and a second end, to provide a fluidic path from the sample port at the first end through the measurement area;

d) a bladder at the second end of the first channel, comprising at least a part of the resilient region in at least the first or second layer and having a volume that is at least about equal to the combined volume of the measurement area and first channel;

e) a stop junction in the first channel between the measurement area and bladder that comprises a co-aligned through-hole in at least the first or second layer, the through-hole being overlaid with a third layer; and f) a second channel having a first end in fluid communication with the first channel at a first point between the sample port and measurement area and a second end vented, in which
   (i) at least the first or second layer has a transparent section at a predetermined second point adjoining the second channel and
   (ii) the volume of the part of the second channel lying between the first and second points is at least about equal to the volume of the measurement area.

The device is particularly well adapted for measuring prothrombin time (PT time), with the biological fluid being whole blood and the measurement area having a composition that facilitates the blood clotting cascade.

DETAILED DESCRIPTION OF THE INVENTION

Figure 1:
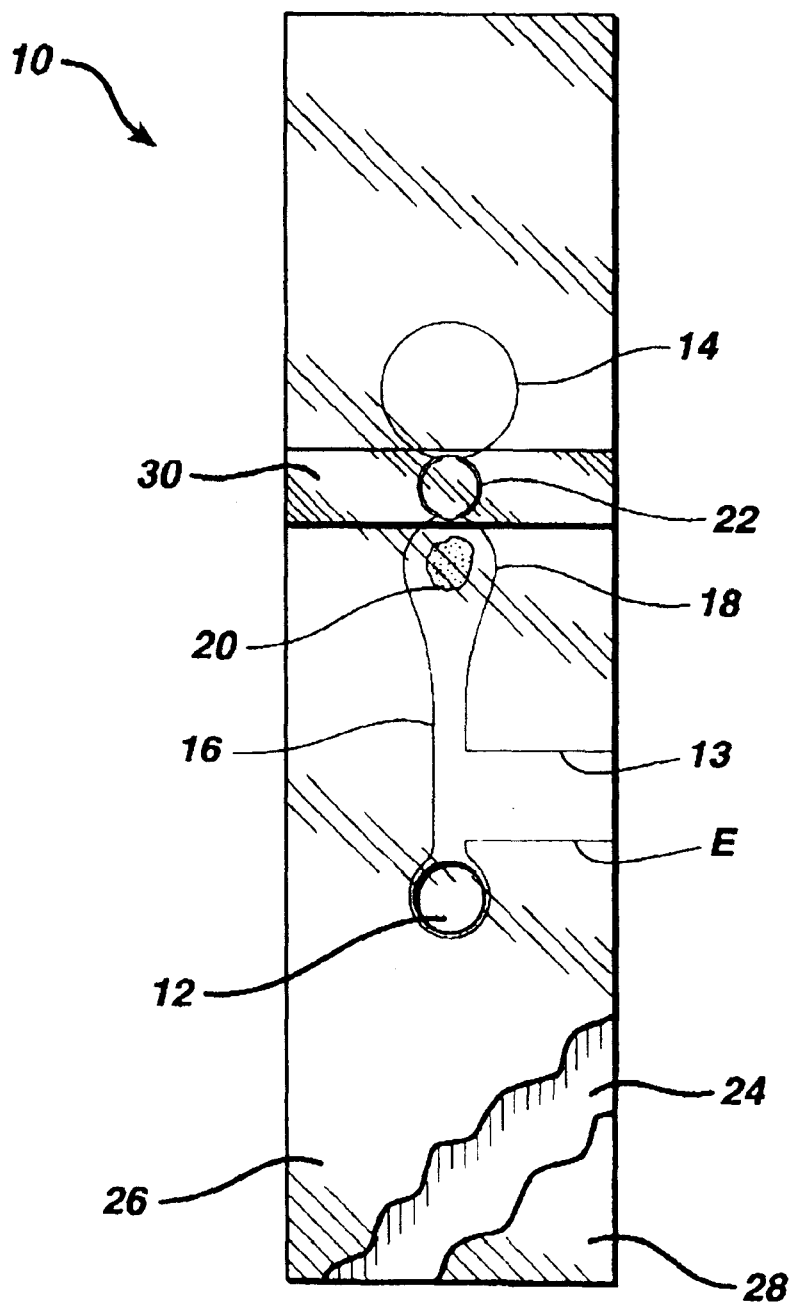
FIG. 1 is a plan view of a device of the present invention.

This invention relates to a fluidic device for analyzing biological fluid. The device is of the type that relates a physical parameter of the fluid, or an element of the fluid, to an analyte concentration in the fluid or to a property of the fluid. Although a variety of physical parameters—e.g., electrical, magnetic, fluidic, or optical—can form the basis for the measurement, a change in optical parameters is a preferred basis, and the details that follow refer to an optical device. The device includes a sample application area; a capillary-fill channel to accumulate at least enough sample to permit a valid measurement to be made; a measurement area, in which the sample may undergo a-change in an optical parameter, such as light scattering; a bladder, to create a suction force to draw the sample from the capillary channel to the measurement area; and a stop junction to stop flow after the measurement area has been filled.

Preferably, the device is substantially transparent over the measurement area, so that the area can be illuminated from one side and the transmitted light measured on the opposite side. The change in transmitted light is a measure of the analyte or fluid property of interest. Alternatively, light that is scattered from a fluid sample or light that passes through the sample and is reflected back through a second time (by a reflector on that opposite side) can be detected by a detector on the same side as the light source.

This type of device is suitable for a variety of analytical tests of biological fluids, such as determining biochemical or hematological characteristics, or measuring the concentration in such fluids of proteins, hormones, carbohydrates, lipids, drugs, toxins, gases, electrolytes, etc. The procedures for performing these tests have been described in the literature. Among the tests, and where they are described, are the following:

(1) Chromogenic Factor XIIa Assay (and other clotting factors as well): Rand, M. D. et al., Blood, 88, 3432 (1996).

(2) Factor X Assay: Bick, R. L. Disorders of Thrombosis and Hemostasis: Clinical and Laboratory Practice. Chicago, ASCP Press, 1992.

(3) DRVVT (Dilute Russells Viper Venom Test): Exner, T. et al., Blood Coag. Fibrinol., 1, 259 (1990).

(4) Immunonephelometric and Immunoturbidimetric Assays for Proteins: Whicher, J. T., CRC Crit. Rev. Clin Lab Sci. 18:213 (1983).

(5) TPA Assay: Mann, K. G., et al., Blood, 76, 755, (1990).; and Hartshorn, J. N. et al., Blood, 78, 833 (1991).

(6) APTT (Activated Partial Thromboplastin Time Assay): Proctor, R. R. and Rapaport, S. I. Amer. J. Clin. Path, 36, 212 (1961); Brandt, J. T. and Triplett, D. A. Amer. J. Clin. Path., 76, 530 (1981); and Kelsey, P. R. Thromb. Haemost. 52, 172 (1984).

(7) HbA1c Assay (Glycosylated Hemoglobin Assay): Nicol, D. J. et al., Clin. Chem. 29, 1694 (1983).

(8) Total Hemoglobin: Schneck et al., Clinical Chem., 32/33, 526 (1986); and U.S. Pat. No. 4,088,448.

(9) Factor Xa: Vinazzer, H., Proc. Symp. Dtsch. Ges. Klin. Chem., 203 (1977), ed. By Witt, I.

(10) Colorimetric Assay for Nitric Oxide: Schmidt, H. H., et al. , Biochemica, 2, 22 (1995).

The present device is particularly well suited for measuring blood clotting time—"prothrombin time" or "PT"—and details regarding such a device appear below. The modifications needed to adapt the device for applications such as those listed above require no more than routine experimentation.

Figure 2:
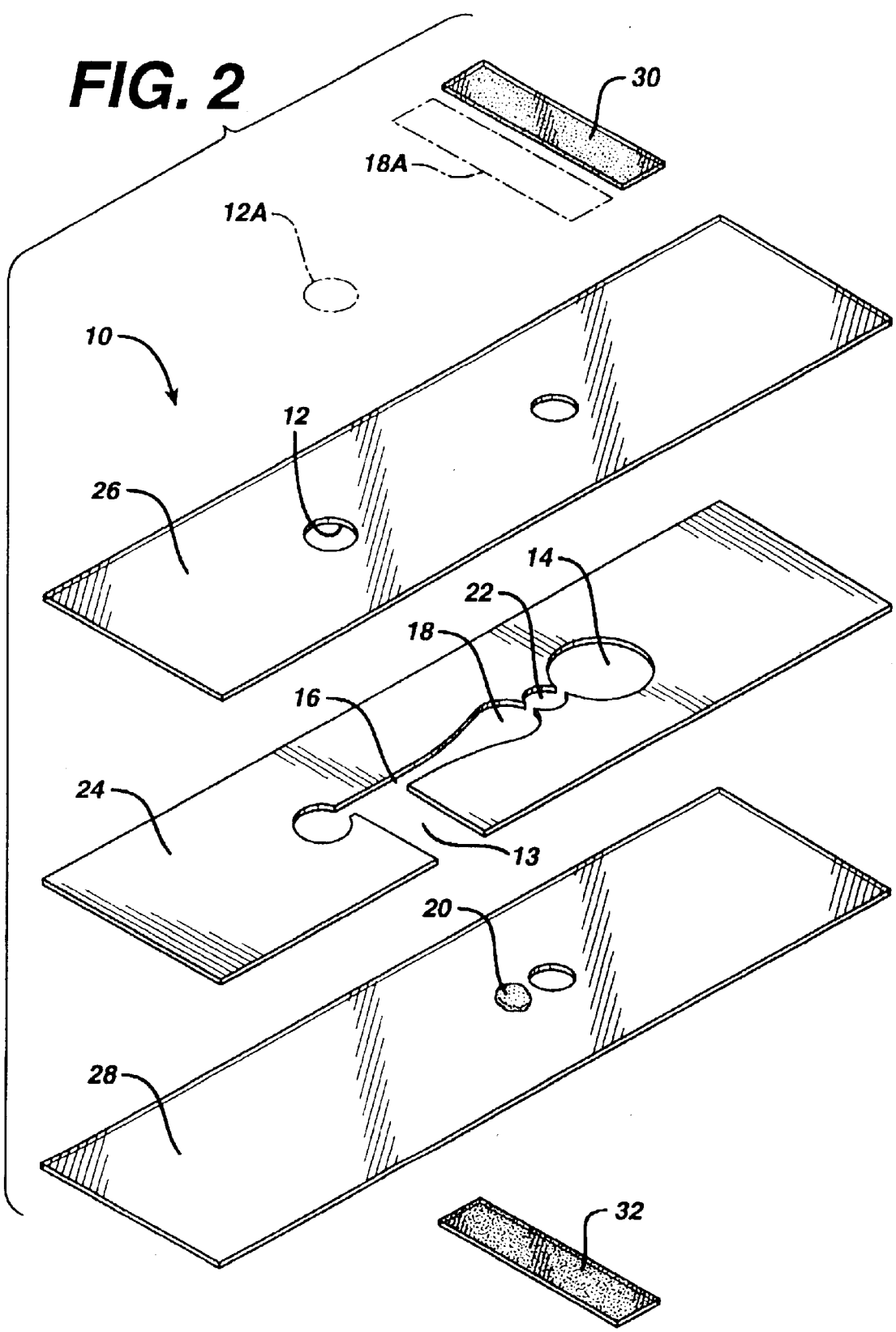
FIG. 2 is an exploded view of the device of FIG. 1.

FIG. 1 is a plan view of a device 10 of the present invention. FIG. 2 is an exploded view and FIG. 3 a perspective view of the device. Blood is applied to sample port 12 after bladder 14 has been compressed. Clearly, the region of layer 26 and/or layer 28 that adjoins the cutout for bladder 14 must be resilient, to permit bladder 14 to be compressed. Polyester of about 0.1 mm thickness has suitable resilience and springiness. Preferably, top layer 26 has a thickness of about 0.125 mm, bottom layer 28 about 0.100 mm. Blood is drawn from port 12 by capillary action into channel 13. It doesn't flow into channel 16, because that path is not vented. Blood continues to flow into channel 13 until it reaches a point at which the volume of blood in channel 13 is at least about equal to the combined volume of measurement area 18 and the volume of channel 16 lying between the measurement area and channel 13. When blood reaches that point—"E" (for "enough-sample") in channel 13—a sensor (described below) senses that enough blood has been drawn into the device and bladder 14 is released. When the bladder is released, suction draws blood from port 12 and channel 13 through channel 16 to measurement area 18. In order to ensure that measurement area 18 can be filled with blood, the volume of bladder 14 is preferably at least about equal to the combined volume of channel 16 and measurement area 18, which preferably contains a reagent 20. If measurement area 18 is to be illuminated from below, layer 28 must be transparent where it adjoins measurement area 18. For a PT test, reagent 20 contains thromboplastin that is free of bulking reagents normally found in lyophilized reagents.

Figure 3:
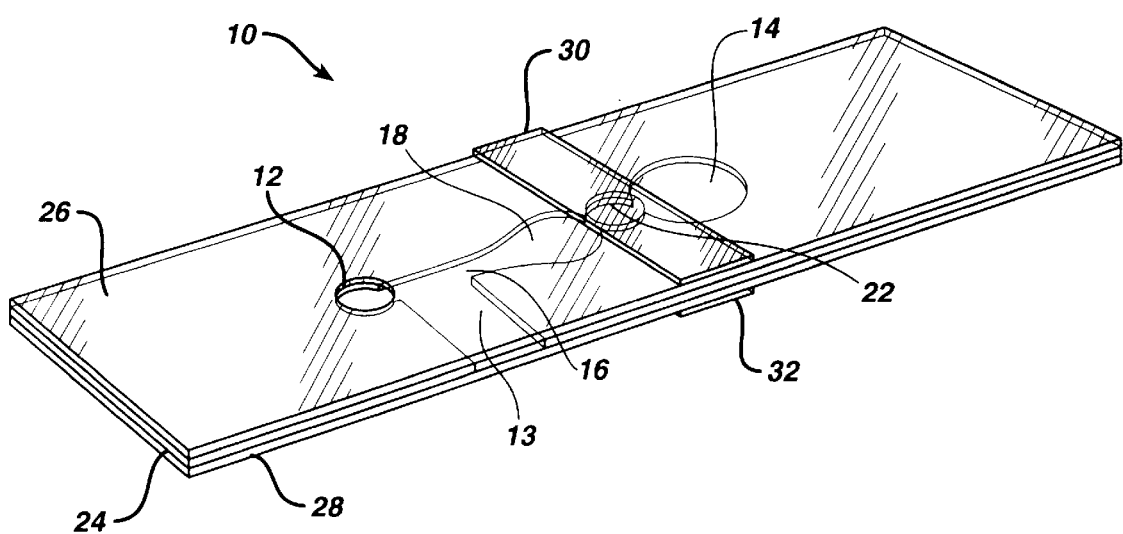
FIG. 3 is a perspective view of the device of FIG. 1.

As shown in FIGS. 1, 2, and 3, stop junction 22 adjoins bladder 14 and measurement area 18; however, a continuation (i.e., "neck") of channel 16 may be on either or both sides of stop junction 22, separating the stop junction from measurement area 18 and/or bladder 14. When the blood reaches stop junction 22, blood flow stops. For PT measurements, it is important to stop the flow of blood as it reaches that point to permit reproducible "rouleaux formation"—the stacking of red blood cells—which is an important step in monitoring blood clotting using the present invention. The principle of operation of stop junctions is described in U.S. Pat. No. 5,230,866, incorporated herein by reference.

As shown in FIG. 2, all the above elements are formed by cutouts in intermediate layer 24, sandwiched between top layer 26 and bottom layer 28. Preferably, layer 24 is double-sided adhesive tape. Stop junction 22 is formed by an additional cutout in layer 26 and/or 28, aligned with the cutout in layer 24 and sealed with sealing layer 30 and/or 32. Preferably, as shown, the stop junction comprises cutouts in both layers 26 and 28, with sealing layers 30 and 32. Each cutout for stop junction 22 is at least as wide as channel 16. Also shown in FIG. 2 is an optional filter 12A to cover sample port 12. The filter may separate out red blood cells from a sample and/or may contain a reagent to interact with the blood to provide additional information. Of course, the filter will offer resistance to passage of the blood sample into sample port 12 and from there into the channels. Thus, a filter must be selected with that in mind. A suitable filter comprises an anisotropic membrane, preferably a polysulfone membrane of the type available from Spectral Diagnostics, Inc., Toronto, Canada. If optional reflector 18A, which may be on or adjacent to a surface of layer 26 and positioned over measurement area 18, is present, the device becomes a transflectance device.

Figure 4:
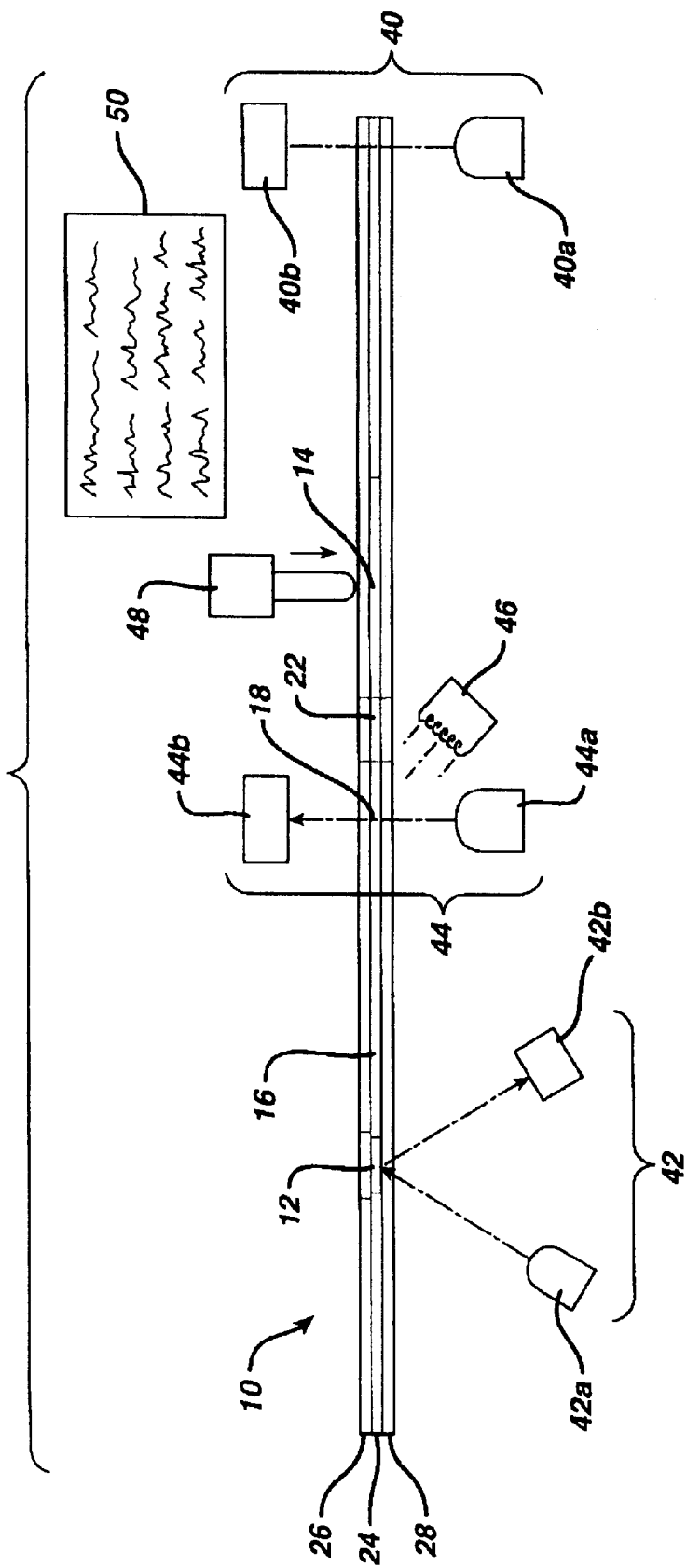
FIG. 4 is a schematic of a meter for use with a device of this invention.

The method of using the strip of FIGS. 1, 2, and 3 can be understood with reference to a schematic of the elements of a meter shown in FIG. 4, which contemplates an automated meter. Alternatively, manual operation is also possible. (in that case, bladder 14 is manually depressed before blood is applied to sample port 12, then released when blood reaches point E on channel 13.) The first step the user performs is to turn on the meter, thereby energizing strip detector 40, enough sample detector 42, measurement system 44, and optional heater 46. The second step is to insert the strip. Preferably, the strip is not transparent over at least a part of its area, so that an inserted strip will block the illumination by LED 40a of detector 40b. (More preferably, the intermediate layer is formed of a non-transparent material, so that background light does not enter measurement system 44.) Detector 40b thereby senses that a strip has been inserted and triggers bladder actuator 48 to compress bladder 14. A meter display 50 then directs the user to apply a blood sample to sample-port 12 as the third and last step the user must perform to initiate the measurement sequence.

Capillary action draws the blood sample into enough sample channel 13, which optionally has a reactant to react with the blood. LED 42a illuminates the edge of channel 13, designated "E" in FIG. 1. When channel 13 is empty; i.e., when no blood extends to point E, background light (e.g., from LED 42a) falls on detector 42b. As blood is drawn into the strip and enters channel 13, the blood at the "enough sample" point, E, changes the amount of light from LED 42a that is reflected to detector 42b, which, in turn, signals actuator 48 to release bladder 14. Depending on the materials of the strip and sample and the geometry of the optics, the light can be either increased or decreased to signal actuator 48. The resultant suction in channel 16 draws blood through measurement area 18 to stop junction 22. Light from LED 44a passes through measurement area 18, and detector 44b monitors the light transmitted through the blood as it is clotting. Analysis of the transmitted light as a function of time (as described below) permits a calculation of the PT time, which is displayed on the meter display 50. Preferably, blood temperature is maintained at about 37° C. by heater 46.

Figure 5:
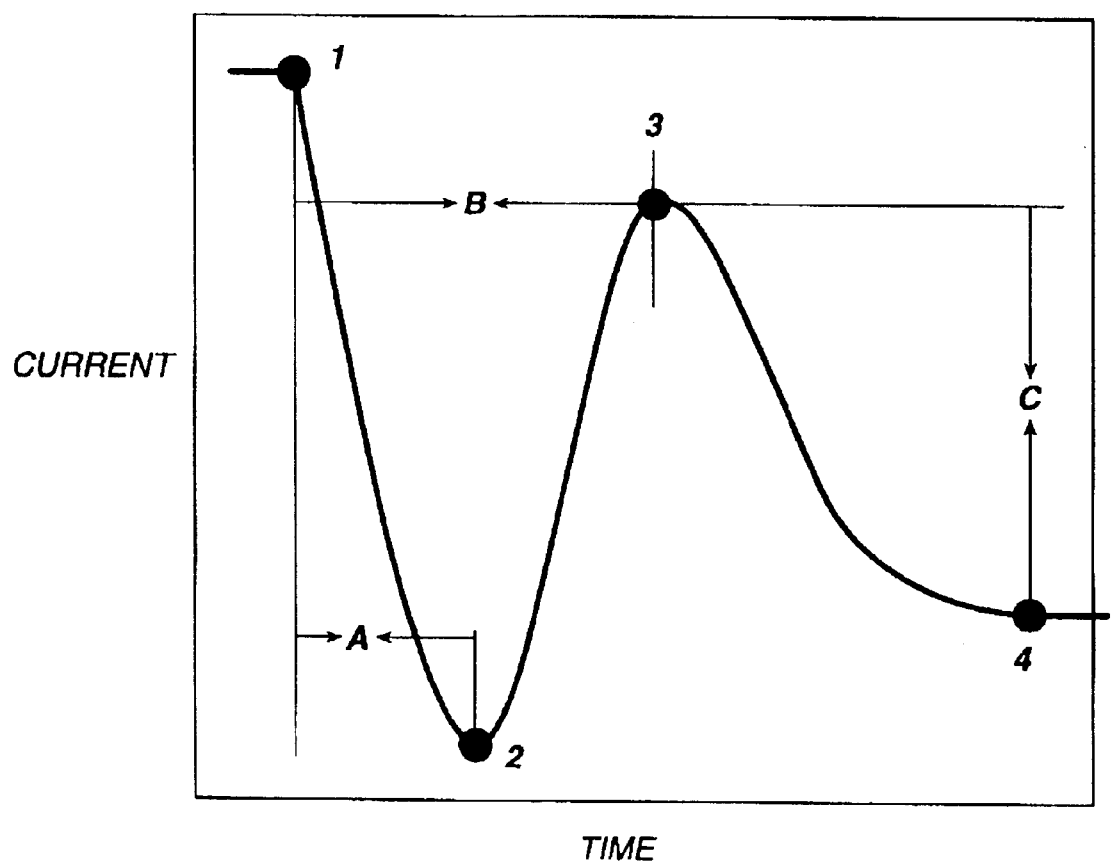
FIG. 5 is a graph of data that is used to determine PT time.

FIG. 5 depicts a typical "clot signature" curve in which the current from detector 44b is plotted as a function of time. Blood is first detected in the measurement area by 44b at time 1. In the time interval A, between points 1 and 2, the blood fills the measurement area. The reduction in current during that time interval is due to Light scattered by red cells and thus an approximate measure of the hematocrit. At point 2, blood has filled the measurement area and is at rest, its movement having been stopped by the stop junction. The red cells begin to stack up like coins (rouleaux formation). The rouleaux effect allows increasing light transmission through the sample (less scattering) in the time interval between points 2 and 3. At point 3, clot formation ends rouleaux formation and transmission through the sample reaches a maximum. The PT time can be calculated from the interval B between points 1 and 3 or the interval between points 2 and 3. Thereafter, blood changes state from liquid to a semi-solid gel, with a corresponding reduction in light transmission. The reduction in current C between the maximum 3 and endpoint 4 correlates with fibrinogen in the sample.

The device pictured in FIG. 2 and described above is preferably formed by laminating thermoplastic sheets 26 and 28 to a thermoplastic intermediate layer 24 that has adhesive on both of its surfaces. The cutouts that form the elements shown in FIG. 1 may be formed, for example, by laser- or die cutting of layers 24, 26, and 28. Preferably, the surface of sheet 28 is hydrophilic (Film 9962, available from 3M, St. Paul, Minn.).

Figure 6:
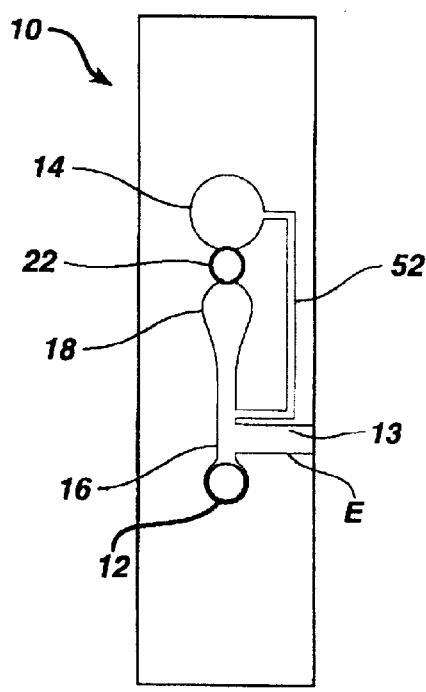
FIG. 6 is a plan view of an alternative embodiment of a device of this invention.

FIG. 6 is a plan view of another embodiment of the device of the present invention, in which the device includes a bypass channel 52 that connects channel 16 with bladder 14. The function and operation of the bypass and "enough sample" channels can be understood by referring to FIGS. 6A–6F, which depict a time sequence during which a blood sample is drawn into device 10 for the measurement.

Figure 6A:
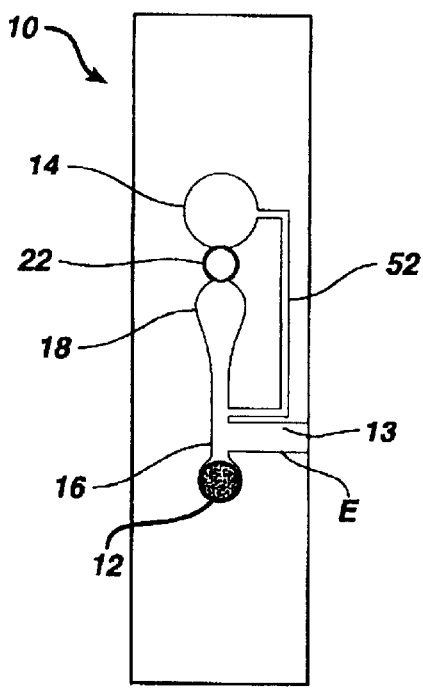
FIGS. 6A–6F depict a time sequence during which a sample is admitted to the device of FIG. 6.

FIG. 6A depicts the situation after a user has applied a blood sample to the strip, while bladder 14 is compressed. This can be accomplished by applying one or more drops of blood to sample port 12.

Figure 6B:
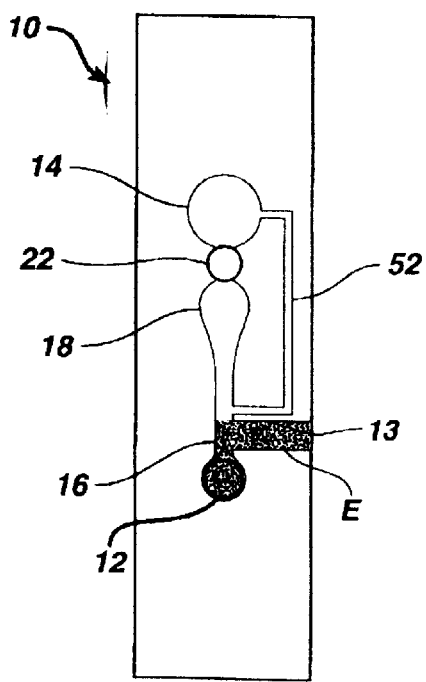

FIG. 6B depicts the situation after blood has been drawn by capillary action into enough-sample channel 13 of the strip and reached point E, thereby triggering release of the bladder and causing reduced pressure in channel 16.

Figure 6C:
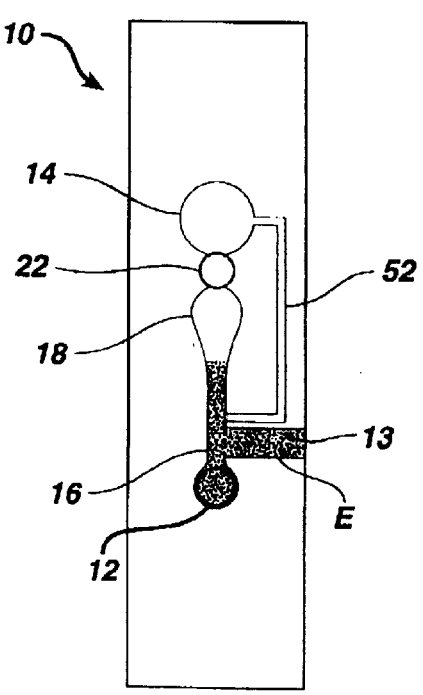

FIG. 6C depicts the situation as blood is drawn into channel 16 from channel 13 and sample port 12. The materials and dimensions of channels 16 and 13 are selected to ensure that blood is preferentially drawn from channel 13, before the blood in port 12 has been depleted.

Figure 6D:
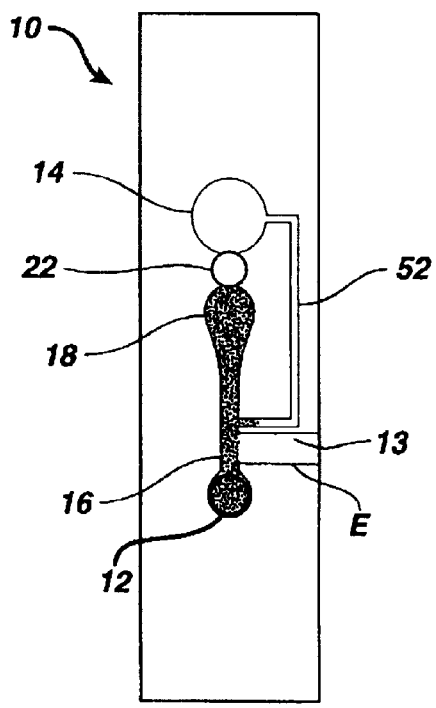

FIG. 6D depicts the situation when the blood sample has been drawn into the measurement area 18. When the blood reaches stop junction 22, it encounters a back pressure that causes it to stop and causes additional blood to be drawn into the bypass channel.

Figure 6E:
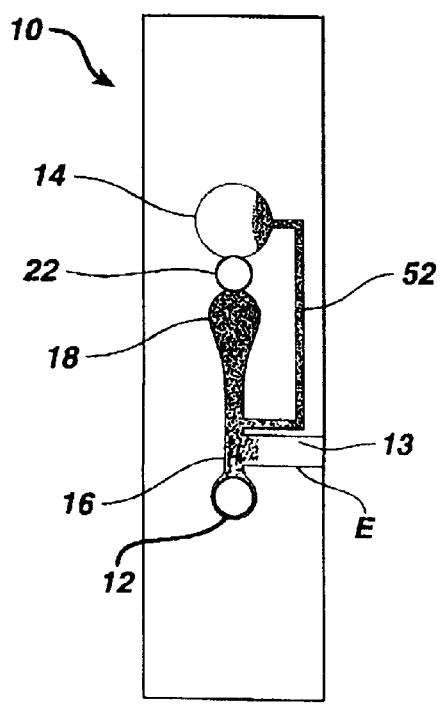

FIG. 6E depicts the "endpoint"; i.e., the situation when a reading is taken. Blood is at rest in measurement area 18. Excess blood has been drawn into bypass channel 52.

Figure 6F:
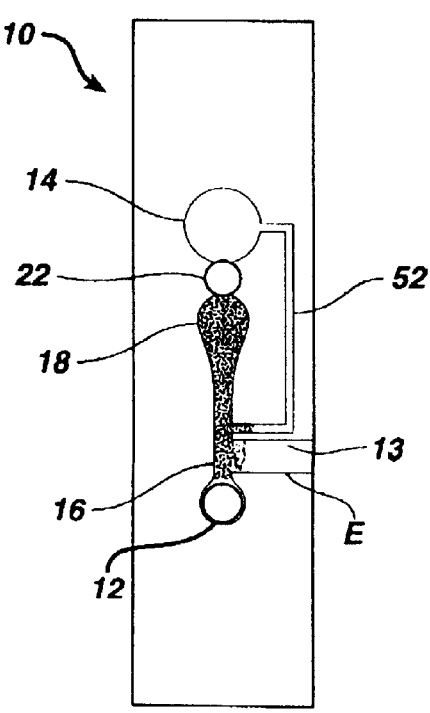

FIG. 6F depicts an alternate endpoint. If the bladder has somewhat less volume and/or has not been completely compressed initially, then a reading is taken when the blood is distributed as shown in FIG. 6F. After ambient pressure has been established in bypass channel 52, excess blood may be drawn from sample port 12 into channel 13 by capillary forces. Note that channel 13 provides a reservoir in which excess sample can accumulate, without affecting the measurement (which is made in measurement area 18).

Figure 7:
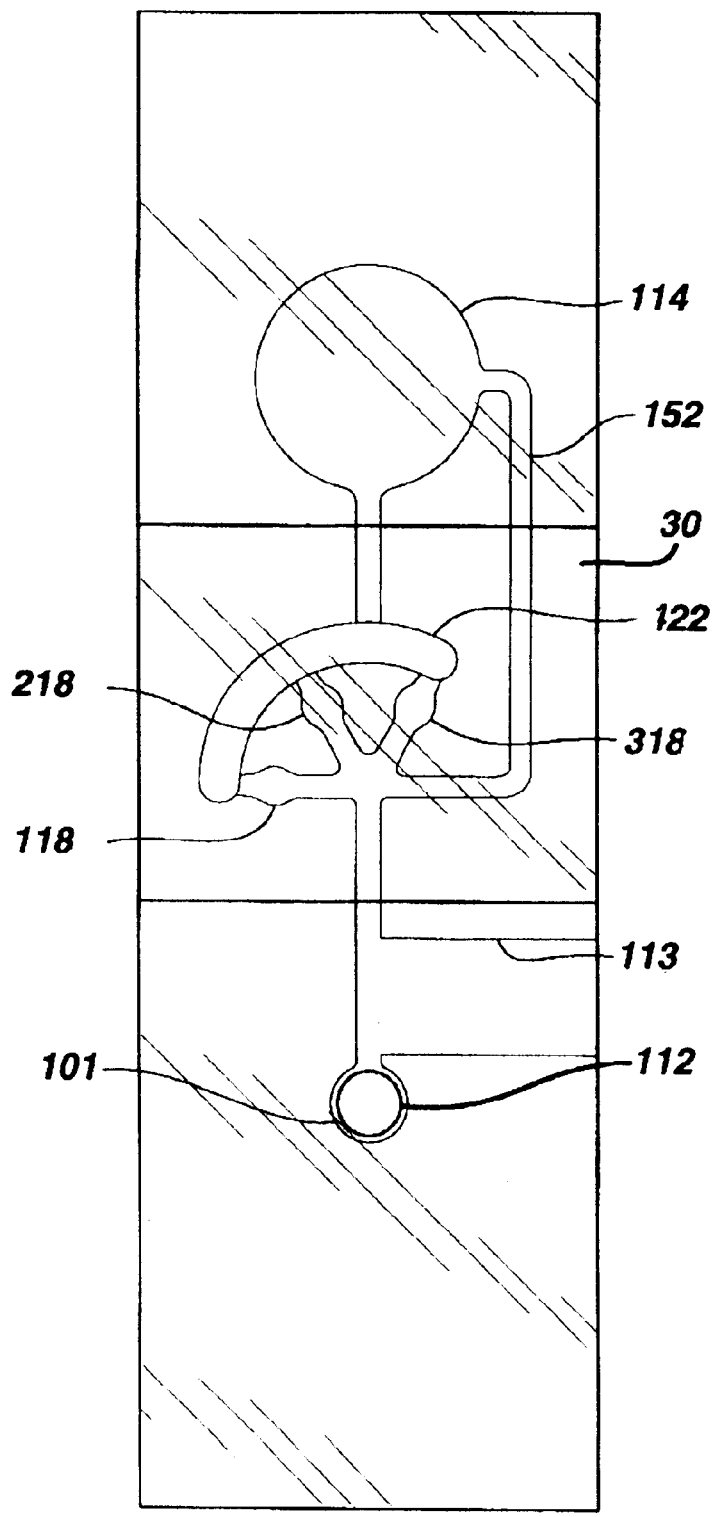
FIG. 7 is a schematic of a device that includes multiple measurement areas, a single bladder, and a single bypass channel.

FIG. 7 depicts a preferred embodiment of the present device. It is a multi-channel device that includes bypass channel 152. Bypass channel 152 serves a purpose in this device that is analogous to that served by bypass channel 52 in the device of FIG. 6, which was described above. Measurement area 118P contains thromboplastin. Preferably, measurement areas 218 and 318 contain controls, more preferably, the controls described below. Area 218 contains thromboplastin, bovine eluate, and recombinant Factor VIIa. The composition is selected to normalize the clotting time of a blood sample by counteracting the effect of an anticoagulant, such as warfarin. Measurement area 318 contains thromboplastin and bovine eluate alone, to partially overcome the effect of an anticoagulent. Thus, three measurements are made on the strip. PT time of the sample, the measurement of primary interest, is measured on area 118. However, that measurement is validated only when measurements on areas 218 and 318 yield results within a predetermined range. If either or both of these control measurements are outside the range, then a retest is indicated. Extended stop junction 122 stops flow in all three measurement areas.

The following examples demonstrate the present invention but are not intended to be in any way limiting.

EXAMPLE 1

Measurement of HbA1c

A device is prepared as described above and as shown in FIGS. 1, 2, and 3. Coated on bottom layer 28, in alignment with sample port 12, is a denaturant/oxidant reagent consisting of $NH_4SCN$, $K_3Fe(CN)_6$, and a buffer. A suspension of anti-HbA1c antibody-latex (Ab-latex) is coated on channel 13 and dried. Measurement area 18 contains polyaspartic acid agglutinator reagent. A blood sample is applied to sample port 12. The denaturant/oxidant causes the red blood cells to lyse and oxidizes the hemoglobin. The treated sample is then drawn into channel 13 by capillary action, where it incubates the Ab-latex. After reaching point E, bladder 14 is released, and sample is drawn into measurement area 18, where the agglutinator reagent stops the reaction. A measurement of the optical transmission of the sample in area 18 yields the HbA1c concentration. More details relating to this type of measurement appear in U.S. Pat. No. 4,847,209, issued on Jul. 11, 1989 to L. A. Lewis et al., incorporated herein by reference.

EXAMPLE 2

Measurement of C-Reactive Protein (CRP)

A device is prepared as described above and as shown in FIGS. 1, 2, and 3. Filter 12A is impregnated with a fluoresceinated liposome suspension and dried. Channel 13 is coated with a solution of complement and dried. The complement is then overcoated with a solution of rabbit anti-CRP antibody and dried. Measurement area 18 is coated with a solution of barbital buffer and EDTA and dried. To run the assay, blood is applied to sample port 12 through filter 12A. Filter 12A retains the erythrocytes but allows plasma to pass. The liposomes in filter 12A resuspend in the plasma and move with it into channel 13, where, at first, the anti-CRP antibody is rehydrated and mixes with the plasma-liposome mixture. The undercoated layer of complement is then exposed to the plasma-liposome-antibody mixture and the complement reaction takes place. Bladder 14 is released and the treated mixture is drawn into measurement area 18, where the barbital buffer/EDTA reagent stops the reaction. Measurement of the fluorescent light output and the output of control(s) (in an area such as area 218 or 318, in FIG. 7) yields the CRP concentration. Details of this measurement appear in *Immunology Methods Manual*, Vol. 1, I. Lefkovitz ed., Basel Institute for Immunology, pp. 548–550, incorporated herein by reference (see also Umeda et al., *J. Immunol. Methods* 95:15–21).

The invention having been fully described, it will be apparent to one of ordinary skill in the art that many modifications and changes may be made to it without departing from the spirit and scope of the present invention.

What is claimed is:

1. A fluidic diagnostic device for measuring an analyte concentration or property of a biological fluid, comprising
   a first layer and second layer, at least one of which has a resilient region over at least a part of its area, separated by an intermediate layer, in which cutouts in the intermediate layer form, with the first and second layers,
   a) a sample port for introducing a sample of the biological fluid into the device;
   b) a measurement area in which a physical parameter of the sample is measured and related to the analyte concentration or property of the fluid;
   c) a first channel, having a first end and a second end, to provide a fluidic path from the sample port at the first end through the measurement area;
   d) a bladder, at the second end of the first channel, comprising at least a part of the resilient region in at least the first or second layer and having a volume that is at least about equal to the combined volume of the measurement area and first channel;
   e) a stop junction in the first channel between the measurement area and bladder that comprises a co-aligned through-hole in at least the first or second layer, the through-hole being overlaid with a third layer; and
   f) a second channel having a first end in fluid communication with the first channel at a first point between the sample port and measurement area and a second end vented, in which
      (i) at least the first or second layer has a transparent section at a predetermined second point adjoining the second channel and
      (ii) the volume of the part of the second channel lying between the first and second points is at least about equal to the volume of the measurement area.

2. The device of claim 1 in which the physical parameter of the sample undergoes a change in the measurement area.

3. The device of claim 1 in which the sample port includes a reactant to react with the sample.

4. The device of claim 3 in which the reactant in the sample port is a denaturant/oxidant.

5. The device of claim 1 in which the second channel includes a reactant to react with a sample drawn into it.

6. The device of claim 5 in which the reactant in the second channel comprises an antibody latex.

7. The device of claim 1 in which the sample port comprises co-aligned through-holes in the first and intermediate layers.

8. The device of claim 1 in which the stop junction further comprises a second through-hole aligned with the first through-hole, the second through-hole being overlaid with a fourth layer.

9. The device of claim 1, further comprising a bypass channel, to provide an additional path from the first channel to the bladder, without traversing the measurement area and stop junction.

10. The device of claim 1 in which at least the first or second layer is substantially transparent adjoining the measurement area and the physical property that is measured is optical transmission through the measurement area.

11. The device of claim 1 further comprising a reflective surface adjoining the measurement area.

12. The device of claim 1 in which the biological fluid is whole blood and the property being measured is prothrombin time.

13. The device of claim 1 in which the measurement area comprises a composition that facilitates blood clotting.

14. The device of claim 13 in which the composition comprises thromboplastin.

15. The device of claim 1 further comprising a filter adjoining the sample port for filtering the biological fluid being introduced into the sample port.

16. The device of claim 15 in which the filter comprises an anisotropic membrane.

17. The device of claim 16 in which the filter material is polysulfone.

18. The device of claim 1 in which the volume of the part of the second channel lying between the first and second points is at least about equal to the combined volume of the measurement area and the volume of the part of the first channel lying between the first point and the measurement area.

19. The device of claim 1 further comprising a bypass channel from the first channel to the bladder and at least one alternate fluidic path from the first channel to the bladder, each such alternate path including a corresponding measurement area and stop junction.

* * * * *